United States Patent
Rymer

(10) Patent No.: US 6,567,613 B2
(45) Date of Patent: May 20, 2003

(54) ELECTRICAL DEVICE FOR EVAPORATING A VOLATILE LIQUID

(75) Inventor: Shaun Rymer, East Yorkshire (GB)

(73) Assignee: Reckitt Benckiser (UK) Limited, Berkshire (GB)

(*) Notice: Subject to any disclaimer, the term of this patent is extended or adjusted under 35 U.S.C. 154(b) by 0 days.

(21) Appl. No.: 10/104,704

(22) Filed: Mar. 22, 2002

(65) Prior Publication Data

US 2002/0146243 A1 Oct. 10, 2002

Related U.S. Application Data

(63) Continuation of application No. PCT/GB00/03663, filed on Sep. 25, 2000.

(30) Foreign Application Priority Data

Sep. 24, 1999 (GB) .............................................. 9922599
Dec. 4, 1999 (GB) .............................................. 9928590

(51) Int. Cl.[7] ................................................. F24F 6/08
(52) U.S. Cl. ..................................... 392/390; 392/395
(58) Field of Search ................................ 392/390, 392, 392/394, 395; 239/34, 44; 261/94, 97, 99, DIG. 65; 122/366

(56) References Cited

U.S. PATENT DOCUMENTS

| | | | |
|---|---|---|---|
| 4,621,768 A | * 11/1986 | Lhoste et al. ............... | 239/44 |
| 4,968,487 A | * 11/1990 | Yamamoto et al. ........ | 422/125 |
| 5,038,394 A | 8/1991 | Hasegawa et al. | |
| 5,095,647 A | 3/1992 | Zobele et al. | |
| 5,222,186 A | * 6/1993 | Schimanski et al. ........ | 392/395 |
| 5,647,053 A | 7/1997 | Schroeder et al. | |
| 6,278,840 B1 | * 8/2001 | Basaganas Millan ....... | 392/390 |
| 6,285,830 B1 | * 9/2001 | Basaganas Millan ....... | 392/395 |

FOREIGN PATENT DOCUMENTS

| | | |
|---|---|---|
| GB | 2 165 154 A | 4/1986 |
| GB | 2 194 442 A | 3/1988 |
| WO | WO 97/28830 A1 | 8/1997 |
| WO | WO 98/19526 A1 | 5/1998 |
| WO | WO 98/58692 A1 | 12/1998 |
| WO | WO 00/10617 A1 | 3/2000 |

* cited by examiner

Primary Examiner—Sang Paik
(74) Attorney, Agent, or Firm—Akin Gump Strauss Hauer & Feld, L.L.P.

(57) ABSTRACT

An electrical device for evaporating a volatile liquid (for example an air freshener) into a room employs a wick (14) which extends upwardly from a container of the volatile liquid. A ring heater (16) is in the vicinity of the end of the wick and assists the evaporation. Vapor escapes from the device through an aperture (10) in a casing above the wick. The vapor emission rate is controlled by a user, who operates a control member in the casing, to alter the vertical position of a tubular body (18). Vapor may flow from the wick to the exterior through the tubular body (18) and then through the aperture (10). However, in all positions of the tubular body vapor may also flow to the aperture, and thence to the exterior, by an auxiliary route, not through the tubular body. It is found that the provision of this auxiliary route for vapor significantly improves the performance of the device. The tubular body (18) may have an upper surface (31) comprising a wall (32) and apertures (33). The wall (32) together with the apertures (33) ensures that any non-evaporated volatile liquid is directed back towards the heater.

12 Claims, 3 Drawing Sheets

ELECTRICAL DEVICE FOR EVAPORATING A VOLATILE LIQUID

CROSS-REFERENCE TO RELATED APPLICATIONS

This application is a continuation of International Application No. PCT/GB00/03663, filed Sep. 25, 2000, which was published in the English language on Mar. 29, 2001, under International Publication No. WO 01/21226 A1, and the disclosure of which is incorporated herein by reference.

BACKGROUND OF THE INVENTION

This invention is directed to a device for evaporating volatile liquids, for example air fresheners and insecticides. The invention relates in particular to a device for evaporating volatile liquids from a container into a room, with the assistance of electrical power.

Devices are known, in which a bottle of volatile liquid has a wick projecting from it, and a heater is located in the vicinity of the distal end of the wick, to accelerate the evaporation of volatile liquid from the wick. The bottle, wick and heater are retained within a casing which carries an electric plug. To operate the heater the device is plugged into a wall socket.

Such devices are known, which purport to offer control of the rate of evaporation of the volatile liquids. In one device, described in Spanish patent application No. 9701388, the rate of evaporation is altered by varying the relative position of the wick and the heater (which typically is ring-shaped). In this patent application there is described a means for moving the container and the wick axially, through the action of a screw thread, while the ring heater is kept stationary.

In one device on the market, the relative movement of a ring heater and a wick is achieved by keeping the wick stationary and moving the heater axially.

In another device on the market, a tiltable barrel device is located at the distal end of the wick. This may be tilted about a horizontal axis to alter the air flow pathways at the distal end of the wick, and thereby alter the rate of evaporation.

However, we have found all such devices to be unsatisfactory in giving good adjustment. Indeed, in our tests we have sometimes found that the rate of evaporation of volatile liquids, when the device is in its minimum setting, to be higher than the rate of evaporation when the device is in its supposed maximum setting.

BRIEF SUMMARY OF THE INVENTION

In accordance with a first aspect of the present invention, there is provided a device for evaporating a volatile liquid, the device comprising:

a container for the volatile liquid;

a wick which has a proximal end region within the container, with the proximal end thereof adjacent to the base of the container, and a distal end region above the container;

an electrical heater able to provide heat to the distal end region of the wick;

a casing which extends over the container and wick, and which has an aperture above the distal end of the wick; and a tubular body in the region between the distal end of the wick and the casing, the tubular body being movable between highest and lowest positions to alter the rate of emission from the device of vapor evaporated from the wick;

wherein the vapor has a flow pathway from the wick to the exterior of the device through the tubular body, and wherein, when the tubular body is in its highest position, the vapor has an auxiliary flow pathway from the wick to the exterior of the device, which auxiliary flow pathway is not through the tubular body.

In accordance with a second aspect of the present invention, there is provided a tubular body forming part of a device for evaporating a volatile liquid, the device comprising:

a container for the volatile liquid;

a wick which has a proximal end region within the container, with the proximal end thereof adjacent to the base of the container, and a distal end region above the container;

an electrical heater able to provide heat to the distal end region of the wick; and a casing which extends over the container and the wick, and which has an aperture above the distal end of the wick;

wherein the tubular body is located in the region between the distal end of the wick and the casing, the tubular body being movable between highest and lowest positions to alter the rate of emission from the device of vapor evaporated from the wick;

wherein the vapor has a flow pathway from the wick to the exterior of the device through the tubular body; and wherein, when the tubular body is in its highest position, the vapor has an auxiliary flow path away from the wick to the exterior of the device, which auxiliary flow path is not through the tubular body.

In our tests of such devices we have found that the highest position of the tubular body is the position at which the evaporation rate is at a maximum. It is better, in this position, to provide such an auxiliary flow pathway than to require that all of the vapor escaping from the device into the exterior must pass through the tubular body.

However, it has been found that in certain conditions, such as when the tubular body is in its highest position, despite the auxiliary flow pathway, which increases the rate of evaporation of the volatile liquid, a portion of the liquid does not evaporate. This non-evaporated liquid escapes from the container, often running down internal surfaces of the container. This can become visible on certain external parts of the container. This is undesirable and unacceptable, as the escaping liquid is unsightly and may cause damage to areas near to the device.

Advantageously, the tubular body comprises an upper surface lying in a plane substantially at right angles to the axis of the tubular body. The surface comprises a wall extending around at least a part of the circumference of the upper surface and extending in a direction substantially perpendicular to the surface and away from the lower end of the tubular body.

The wall acts as a dam redirecting any non-evaporated liquid towards the heater in order that the liquid may be reheated. The presence of the wall thus ensures that any non-evaporated liquid is returned towards the heater where it is heated again. This process eliminates or at least significantly reduces the portion of volatile liquid which does not eventually evaporate during the heating process, and substantially eliminates liquid from becoming visible on certain external parts of the container.

Alternatively, or in addition, the tubular body contains one or more apertures formed in the upper surface. The one or more apertures allow liquid to escape towards the heater.

The surface may be substantially the same size and shape as the cross sectional area of the tubular body, but preferably, the upper surface has a greater radius than that of the cross sectional area of the tubular body.

Preferably, the upper surface is positioned co-axially with the tubular body. Because the upper surface of the tubular body is larger in area than the cross-sectional area of the tubular body, an upper surface is created. The upper surface extends horizontally beyond the tubular body and provides a greater catchment area for non-evaporated liquid, thus reducing further the portion of non-evaporated liquid which is able to escape from the device.

In one embodiment, the upper region of the casing may be provided with one or more separate openings, in addition to the aperture which is above the distal end of the wick. For example, there may be an array of openings around the aperture, so that the top of the casing has one aperture and further openings, preferably smaller openings, of "pepper-pot" type.

In another embodiment, there may be a space between the upper end of the tubular body and the casing, in the highest position of the tubular body, through which space vapor may flow. Thus, the auxiliary flow pathway may be past the lower end of the tubular body, up the outside of the tubular body, over the upper end of the tubular body, through the space, and out through the aperture above the tubular body. Such embodiments have been shown to be very effective and are preferred embodiments of the present invention.

A further advantage of the wall-forming part of the upper surface of the tubular body, in a preferred embodiment of the invention, is that the wall prevents the upper end of the tubular body from making contact with the casing, thus ensuring that there is a space between the upper end of the tubular body and the casing in the highest position of the tubular body. This enhances evaporation of the volatile liquid.

The space between the upper end of the tubular body and the casing may be an annular space. Stops may be provided to prevent the tubular body reaching the casing in the highest position.

Alternatively, the device may be such that the tubular body contacts the casing in the highest position of the tubular body, with one or more openings being provided, in the upper region of the tubular body or in the part of the casing which contacts the tubular body. Such an opening is suitably of cut-out shape, by which we mean it extends to the end of the respective part.

In one embodiment, the upper end of the tubular body may suitably have one or more openings of cut-out shape. Thus, it may be of castellated form. Alternatively, a downwardly dependent skirt may project from said aperture, and the skirt may have one or more openings, suitably of cut-out shape. Thus, the skirt may be of castellated form, with the castellations facing in the downward direction.

Preferably, the aperture in the casing above the distal end of the wick is of substantially the same size and shape as the tubular body, in horizontal cross section.

Suitably, the ratio of the cross-sectional area of the space or opening, or the openings in total when there is more than one, to the transverse cross-sectional area of the flow pathway within the tubular body, is in a range of about 1:5 to about 5:1, preferably about 1:3 to about 3:2, more preferably about 1:2 to about 1:1, and especially about 6:10 to about 9:10. In devices in which the size of the space or of the opening(s) is at a minimum when the tubular body is in its highest position, these ratios refer to the situation when the tubular body is in its highest position.

There is a gap between the lower end of the tubular body and the heater, at least when the tubular body is in its highest position. Such a gap is preferably smaller in cross-sectional area than the horizontal cross-sectional area of the flow pathway within the tubular body. The ratio thereof may suitably be no more than about 1:2, preferably no more than about 1:5, most preferably no more than about 1:10. Such a gap is suitably smaller in area than the area of the opening, or of the openings in total when there is more than one. The ratio thereof may suitably be no more than about 1:2, preferably no more than about 1:5, most preferably no more than about 1:10.

Preferably, the heater and the wick are in fixed positions in the casing.

An important feature of this invention is that there be provided an auxiliary flow pathway when the tubular body is in its highest position. Such an auxiliary flow pathway is preferably also provided in all other positions of the tubular body, including in its lowest position.

A further important feature of this invention is that a means is provided for allowing non-evaporated volatile liquid to be redirected back towards the heater.

Suitably the heater is a ring heater, as is conventional, and the wick is aligned with the central axis of the ring heater. Preferably, the distal end region of the wick is within the hole defined by the ring heater. Suitably, the ring heater comprises an electrical resistor. Preferably, it is a thermistor. Preferably, it is powered by mains electricity, and the device is provided with plug formations to enable it to be operated from a mains electrical socket.

When a device is provided with plug formations and has the one or more openings in the upper end of the tubular body or in the lower end of a downwardly dependent skirt, preferably there is such an opening in the side of the tubular body or skirt facing toward the plug formations (i.e., the side nearest the plug formations). Preferably, there are two further openings centered on positions spaced about 90° around the circumference from the center of the opening on the side which faces toward the plug formations. Preferably, there is also such an opening on the side facing away from the plug formations (i.e., farthest from the plug formations). Thus, in especially preferred embodiments there are at least four such openings.

Preferably, the tubular body does not overlie the distal end of the wick, even in the lowest position of the tubular body. Suitably, the tubular body is within a hole defined by the ring heater, even in its lowest position. Preferably, the lower end of the tubular body is substantially in the plane of the upper surface of the ring heater, when the tubular body in its highest position. Preferably, the lower end of the tubular body is above the distal end of the wick, even in the lowest position of the tubular body.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 4:
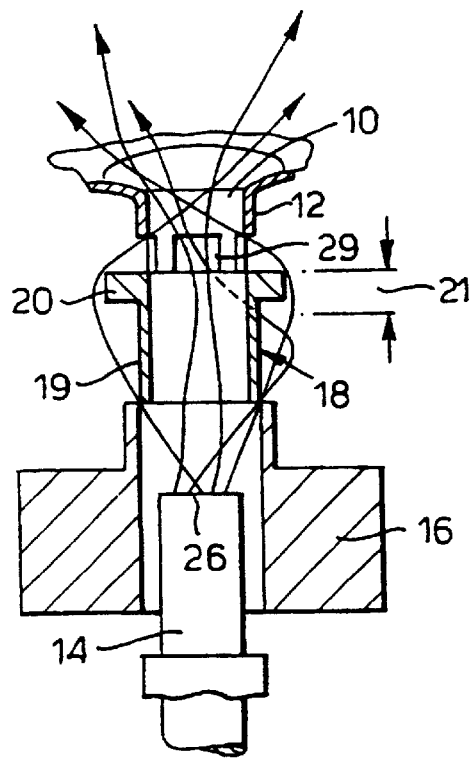
FIG. 4 is a sectional view through line 4–4' in FIG. 2, showing the upper region of the device set for its maximum vapor emission rate.

The device of FIGS. 1 to 4 has a container in the form of a replaceable glass bottle 2 containing a volatile air freshener liquid, and a plastic casing 4 which extends over the opening of the container, and also behind it. From the rear wall of the container above the casing 4 extends an electrical plug 6. In this embodiment it is a British-style three-pin plug, but of course for other countries the appropriate plug will be employed, often a two-pin plug. The top of the casing 4 is, for aesthetic reasons, somewhat downwardly inclined in the forward direction, such that the casing terminates in a discrete slanted top face 8. Within the slanted top face 8 there is a generally circular central aperture 10, defined by a downwardly depending skirt 12. Projecting vertically upwards from the container is a cylindrical wick 14, the distal end region of which is shown in FIG. 4. The diameter of the wick is 6.8 mm. The proximal end of the wick is within the container adjacent to its bottom. Adjacent to the distal end region of the wick is a positive temperature coefficient (PTC) thermistor. The wick 14, the ring heater 16 and the aperture 10 are all axially aligned.

There is a space between the ring heater 16 and the lower end of the skirt 12, and within this space there is located a tubular body 18. The tubular body 18 has an annular cylindrical wall 19 and, at its top end, a collar 20. Its bore is circularly cylindrical from end to end, and the bore diameter is 8.4 mm. The tubular body 18 has its axis aligned with the axis of the aperture, wick and ring heater. The tubular body 18 may be moved up and down under the control of the user with a traverse indicated by the double-headed arrow 21 in FIG. 4. The tubular body 18 is connected via a connecting body (not shown in the drawings, for clarity) to a control member 22 exposed to the exterior, and constrained to move within an inclined guideway 23 in the casing.

Figure 1:
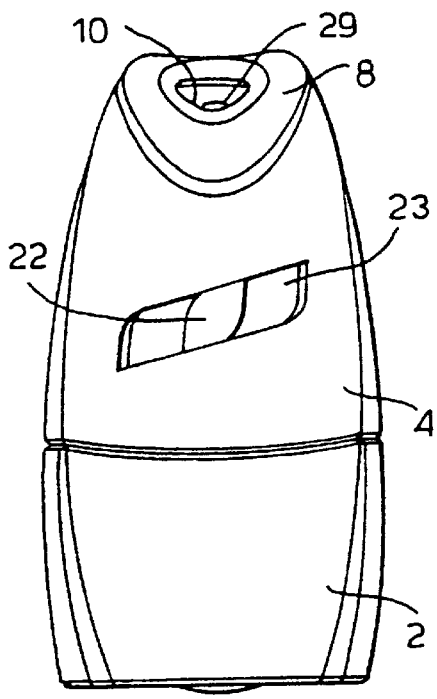
FIG. 1 is a front view of a device of a first embodiment in accordance with the invention.
Figure 2:
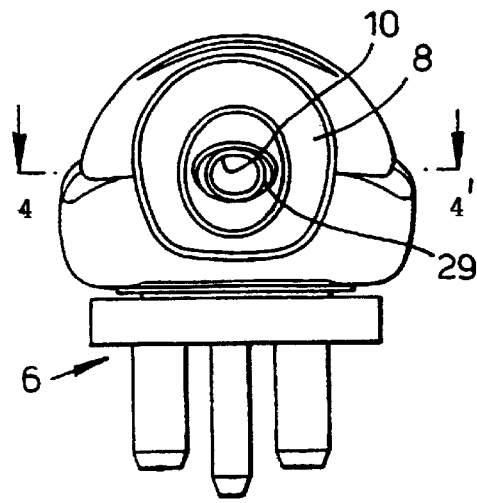
FIG. 2 is a plan view of the device of FIG. 1.
Figure 3:
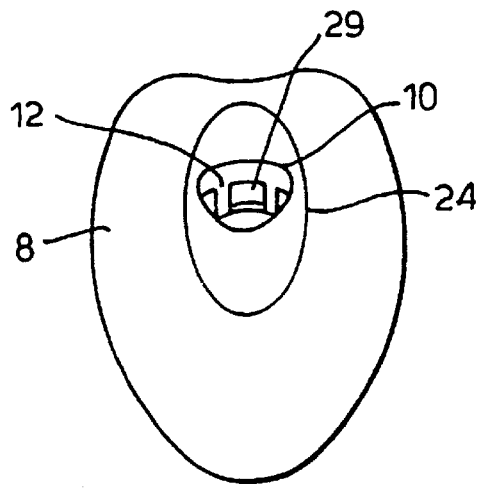
FIG. 3 is a perspective view of the upper region of the device of FIG. 1.

When the control member 22 is in its highest position within the guideway 23 (at the right-hand end of the guideway as shown in FIG. 1), the tubular body 18 is located in its highest position, as shown in FIG. 4. In this position the delivery of vapor from the wick to the exterior of the device is at its maximum. When the control member 22 is in its lowest position (at the left-hand end of the guideway shown in FIG. 1), the tubular body 18 is at its lowest position in FIG. 4, with the top of the tubular body at the level of the bottom arrow head of arrow 21. Delivery of vapor in this position is at a minimum.

The slanted top face 8 of the casing is molded with an oval depression around the opening 10, for aesthetic reasons. The boundary 24 of this oval depression is shown most clearly in FIG. 3.

The wick 14 is vertical in use and its circular distal end 26 is horizontal. Its distal end 26 is located in the hole defined by the ring heater 16. It will be apparent from FIG. 4 that even in the lowest position of the tubular body 18, it does not pass over the wick 14. In the highest position of the tubular body 18 the plane of its lower end is substantially in the plane of the upper surface of the ring heater 16. In other positions of the tubular body 18 its lower end is in the hole defined by the ring heater. The external diameter of the wall 19 of the tubular body is 9.8 mm, and the diameter of the cylindrical hole within the ring heater is 9.9 mm. Thus, any vapor rising under convection from the wick and not passing through the bore of the tubular body 18 has an annular gap of 0.1 mm thickness to pass through. The area of this gap is approximately 1.5 mm$^2$. Thus, in all positions of the tubular body vapor evaporating from the wick can pass through the tubular body, or can pass through the gap between the tubular body and the ring heater.

The downwardly depending skirt 12, which defines a generally cylindrical passageway leading to the circular aperture 10, has four openings 29 of cut-out shape, extending to the bottom of the skirt. Each opening shown in FIG. 4 is 4 mm wide and 3 mm high. The other opening, not shown, which is in the side of the skirt facing away from the plug (i.e., farthest from the plug) is 4 mm wide and 1 mm high. The position of all four openings may just be seen, marked in black, in FIG. 2. The openings are centered on positions spaced 90° around the circumference from each other.

It will be apparent that when the device is set to its maximum vapor emission rate, with the tubular body at its highest position as shown in FIG. 4, vapor can pass to the aperture 10 through the tubular body, or can by-pass it, by flowing through the gap between the lower end of the tubular body and the upper end of the ring heater, up outside the tubular body, and then enter the aperture via the openings 29. The pathways by which vapor can flow to the exterior of the device are marked with arrows in FIG. 4.

We have found that enabling vapor to leave the device by an auxiliary flow pathway, not through the tubular body, brings about a marked improvement in operation of the device, in particular in preventing the condensation of vapor within the device.

Figure 5:
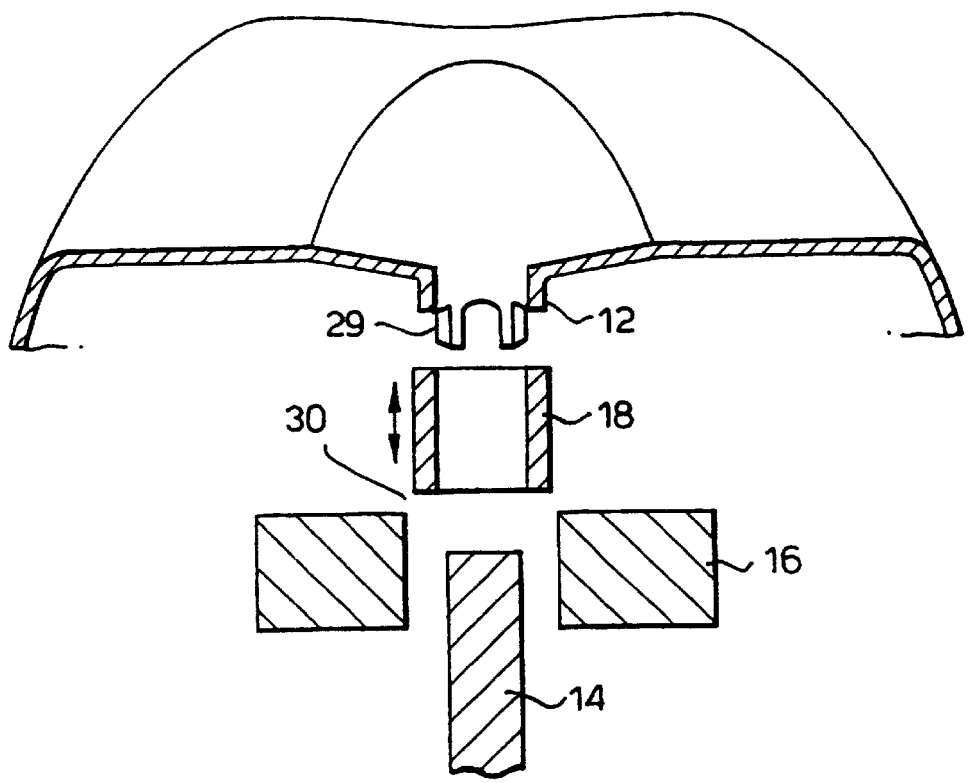
FIG. 5 is a schematic sectional view of the upper region of a second embodiment of a device in accordance with the invention, set for an intermediate vapor emission rate.

In a second embodiment shown in FIG. 5 the tubular body 18 is a simple circular cylinder and the heater 16 is of simpler design, but it provides an auxiliary flow pathway in the same manner as the first embodiment. However, there are only three openings 29, the ones visible in FIG. 5. There is no opening in the side of the skirt facing away from the plug (i.e., farthest from the plug). The tubular body 18 of the FIG. 5 embodiment is shown in an intermediate position. It will be apparent that the gap 30 between the ring heater 16 and the tubular body 18 in this intermediate position (and in higher positions) is larger than in the first embodiment.

In a further embodiment (not shown) the downwardly depending skirt does not have any apertures, but terminates in a circular face. Thus, the skirt seals against the tubular body, in the highest position of the latter. Instead, the upper end of the tubular body is castellated, and so has apertures, preferably four, of cut-out shape.

Figure 6:
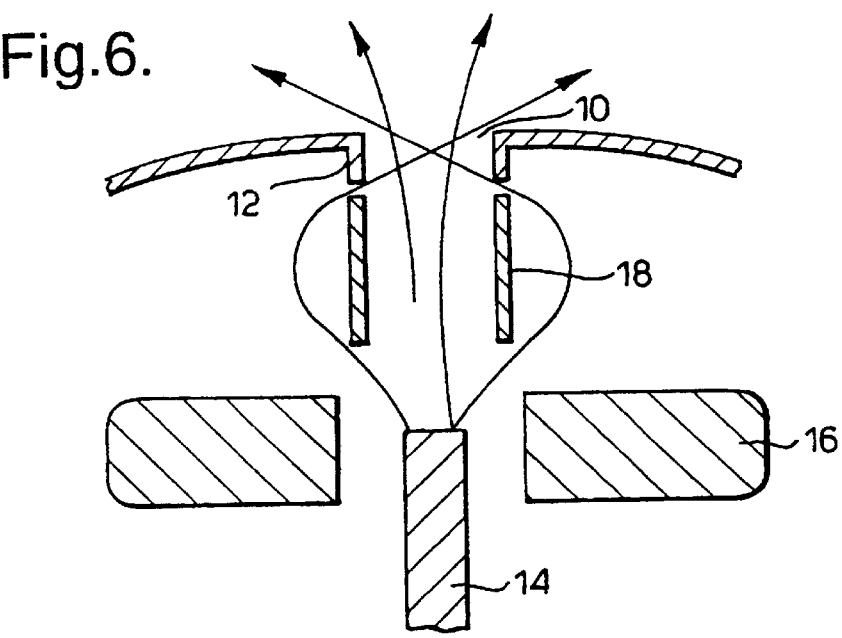
FIG. 6 is a schematic sectional view of a third embodiment of a device in accordance with the invention, set for its maximum vapor emission rate.

A further embodiment is shown in FIG. 6. In this embodiment the downwardly depending skirt 12 is not castellated, nor is the upper end of the tubular body 18 castellated. Rather, in the highest position of the tubular body 18, shown in FIG. 6, it is slightly spaced from the lower end of the downwardly depending skirt 12. This may be achieved simply by designing the device so that that a space is left, when the control member 22 abuts the upper end of the guideway 23. Thus, an annular space is part of the auxiliary flow pathway for vapor. The pathways by which vapor can flow to the exterior of the device are marked with arrows in FIG. 6.

Figure 7:
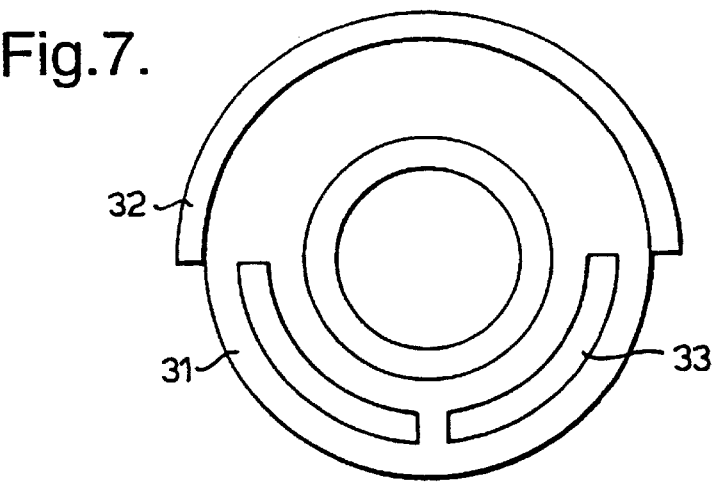
FIG. 7 is a schematic top view of the upper surface of the tubular body according to the second aspect of the present invention and forming part of the devices shown in FIGS. 1 to 6.
Figure 8:
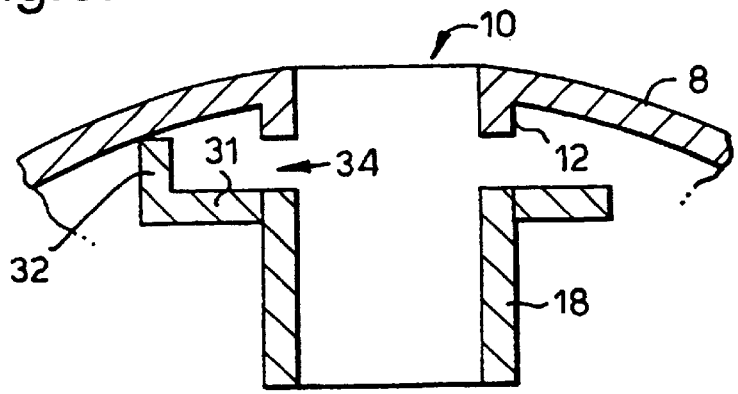
FIG. 8 is a schematic sectional view of the tubular body of FIG. 7 from one side, showing its position relative to the slanted top face of the casing.

Referring to FIGS. 7 and 8, a further embodiment of the tubular body 18 is shown. The tubular body 18 comprises an upper surface 31 lying in a plane substantially at right angles to the axis of the tubular body 18. The upper surface 31 comprises a wall 32 which extends above the upper surface 31 substantially at right angles to the upper surface 31. The wall 32 extends partially around the circumference of the upper surface 31. The upper surface further comprises one or more apertures 33. Although two apertures are shown in the embodiment illustration FIGS. 7 and 8, any other number of apertures could also be used.

It has been found that in certain positions of the tubular body 18, particularly when the tubular body is at its highest position, a certain portion of volatile liquid does not evaporate and therefore remains in liquid form. The upper surface 31 serves to catch non-evaporated liquid. The wall 32 serves as a dam directing the caught liquid through the tubular body 18 or through the apertures 33 and back towards the heater. The non-evaporated liquid is then heated up again and may now evaporate. Any liquid which does not evaporate is again directed back towards the heater due to the presence of the dam 32 and the apertures 33. Through this reiterative process, eventually most, if not all, of the liquid will evaporate, thus overcoming the problem of non-evaporated liquid escaping from the device.

The upper surface 31 of the tubular body 18 extends beyond the outer surface of the tubular body and therefore provides a large catchment area for non-evaporated liquid. The wall 32, as well as serving as a dam for non-evaporated liquid, also serves to ensure that there is always a gap 34 between the casing skirt 12 and the upper surface 31 of the tubular body. This arrangement further enhances the auxiliary flow paths and increases ventilation within the device. This ensures greater evaporation of the volatile liquid.

In a further embodiment (not shown) there are no openings defined as between the tubular body and the downwardly depending skirt, and these parts abut in the highest position of the tubular body, so that no flow pathway is defined between them. Instead, openings are provided in the slanted top face 8 of the casing, around the central aperture 10. Preferably, there are twelve such openings, in a circular array.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A device for evaporating a volatile liquid, the device comprising:

a container for the volatile liquid;

a wick which has a proximal end within the container, with the proximal end adjacent to a base of the container, and a distal end above the container;

an electrical heater able to provide heat to the distal end of the wick;

a casing which extends over the container and the wick, the casing having an aperture above the distal end of the wick; and a tubular body in a region between the distal end of the wick and the casing, the tubular body being movable between highest and lowest positions to alter a rate of emission from the device of vapor evaporated from the wick;

wherein the vapor has a flow pathway from the wick to an exterior of the device through the tubular body, and wherein, when the tubular body is in the highest position, the vapor has an auxiliary flow pathway from the wick to the exterior of the device, which auxiliary flow pathway is not through the tubular body.

2. The device as claimed in claim 1, wherein the auxiliary flow pathway leads vapor to said aperture.

3. The device as claimed in claim 1, wherein there is a space between an upper end of the tubular body and the casing, in the highest position of the tubular body, and the space is part of the auxiliary flow pathway.

4. The device as claimed in claim 3, wherein, in the highest position of the tubular body, a ratio of a cross-sectional area of the space to a cross-sectional area of the aperture is in a range about 1:5 to 5:1.

5. The device according to claim 1, wherein the tubular body comprises an upper surface lying in a plane substantially perpendicular to a longitudinal axis of the tubular body, the upper surface having a wall extending substantially perpendicularly from the upper surface around at least part of a circumference of the upper surface and extending in a direction away from a lower end of the tubular body.

6. The device according to claim 5, wherein the tubular body contains at least one aperture formed in the upper surface.

7. The device as claimed in claim 1, wherein a downwardly dependent skirt projects from said aperture, wherein a lower end of the skirt has at least one opening of cut-out shape, and wherein in the highest position of the tubular body an upper end of the tubular member abuts the lower end of the skirt.

8. The device as claimed in claim 7, wherein the lower end of the skirt is of inverted castellated form, having a plurality of openings of cut-out shape.

9. The device as claimed in claim 1, wherein an upper end of the tubular body has at least one opening of cut-out shape, and wherein in the highest position of the tubular member the upper end of the tubular member abuts the casing.

10. The device as claimed in claim 9, wherein the upper end of the tubular body is of castellated form, having a plurality of openings of cut-out shape.

11. The device as claimed in claim 1, wherein there is provided an array of openings around the aperture, providing a part of the auxiliary flow pathway.

12. The device as claimed in claim 11, wherein, in the highest position of the tubular body, a ratio of a cross-sectional area of the openings to a cross-sectional area of the aperture is in a range about 1:5 to 5:1.

* * * * *